United States Patent [19]

Bryant et al.

[11] Patent Number: 5,624,940
[45] Date of Patent: Apr. 29, 1997

[54] AQUEOUS SOLUTION INCLUSION COMPLEXES OF BENZOTHIOPHENE COMPOUNDS WITH WATER SOLUBLE CYCLODEXTRINS, AND PHARMACEUTICAL FORMULATIONS AND METHODS THEREOF

[75] Inventors: Henry U. Bryant, Indianapolis; George J. Cullinan, Trafalgar; Paul C. Francis; David E. Magee, both of Indianapolis; Stephanie A. Sweetana, Bloomington; Arvind L. Thakkar, Indianapolis, all of Ind.

[73] Assignee: Eli Lilly and Company, Indianapolis, Ind.

[21] Appl. No.: 497,327

[22] Filed: Jun. 30, 1995

Related U.S. Application Data

[63] Continuation of Ser. No. 166,788, Dec. 14, 1993, abandoned.

[51] Int. Cl.$^6$ .......................... A61K 31/40; A61K 31/445; A61K 47/40
[52] U.S. Cl. .......................... 514/324; 514/443; 514/444; 514/448; 514/777; 514/950; 424/488
[58] Field of Search ........................ 514/324, 777, 514/950, 448, 443, 444; 424/488

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 4,727,064 | 2/1988 | Pitha | 514/58 |
| 4,764,604 | 8/1988 | Müller | 536/103 |
| 5,015,648 | 5/1991 | Humphrey et al. | 514/317 |
| 5,019,563 | 5/1991 | Hunter et al. | 514/58 |
| 5,043,326 | 8/1991 | Stadler née Szoke et al. | 514/58 |
| 5,089,482 | 2/1992 | Hermans et al. | 514/58 |
| 5,101,065 | 3/1992 | Skuballa et al. | 514/58 |
| 5,134,127 | 7/1992 | Stella et al. | 514/58 |
| 5,229,370 | 7/1993 | Ammeraal | 514/26 |
| 5,393,763 | 2/1995 | Black et al. | 514/333 |
| 5,464,845 | 11/1995 | Black et al. | 514/326 |

FOREIGN PATENT DOCUMENTS

| | | |
|---|---|---|
| WO85/02767 | 7/1985 | WIPO |

OTHER PUBLICATIONS

Draper, et al., "Effects of Raloxifene (LY139481 HC1) on Biochemical Markers of Bone and Lipid Metabolism in Healthy Postmenopausal Women", Hong Kong, Fourth Int'l. Symp. on Osteoporosis, Mar. 29, 1993.

Bryant, et al., "Protection from Bone Loss and Lowering of Serum Cholesterol in the Absence of uterine Stimulation in Overiectomized Rats", Am. Soc. Bone & Min., Tampa, Sep. 18–22, 1993.

*Inclusion Compounds*, 3(11):333–389, Atwood, J.L., et al., (eds.), Academic Press (1984).

*Controlled Drug Delivery*, 5:125–148, Pitha, J., et al., Bruck S.D., (ed), CRC Press (1983).

Draper et al, "Effects of raloxifene . . . on biochemical markers of bone . . . " 4th Internat'l Symp. on Osteoporosis. Mar. 29, 1993.

Szejtli, "Industrial Applications of Cyclodextrins" Ch. 11 of *Inclusion Compounds* v. 3, Atwood et al, ed. Acad. Pr., 1984. pp. 331–389.

*Primary Examiner*—S. Mark Clardy
*Attorney, Agent, or Firm*—Janelle D. Strode; David E. Boone

[57] ABSTRACT

The present invention provides aqueous inclusion complexes of certain known benzothiophene compounds, particularly Raloxifene, and water soluble cyclodextrins. Also provided are pharmaceutical compositions of such inclusion complexes, and methods of using these complexes for inhibiting bone loss and reducing serum cholesterol in mammals.

16 Claims, No Drawings

AQUEOUS SOLUTION INCLUSION COMPLEXES OF BENZOTHIOPHENE COMPOUNDS WITH WATER SOLUBLE CYCLODEXTRINS, AND PHARMACEUTICAL FORMULATIONS AND METHODS THEREOF

This application is a continuation of prior application Ser. No. 08/166,788, filed on Dec. 14, 1993 now abandoned.

BACKGROUND OF THE INVENTION

This invention relates to the fields of pharmaceutical and organic chemistry and provides novel inclusion complexes, and pharmaceutical formulations thereof, which are useful for the treatment of certain medical indications in mammals.

Benzothiophenes of formula I

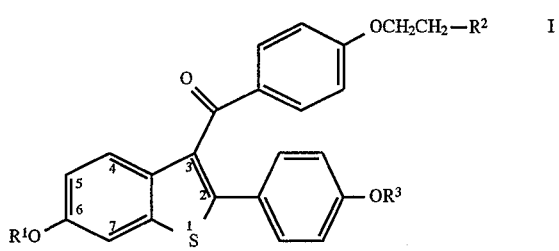

wherein $R^1$ and $R^3$ each are independently hydrogen, $C_1$-$C_4$ alkyl, —CO—($C_1$-$C_6$ alkyl), or —CO—Ar in which Ar is optionally substituted phenyl; and $R^2$ is selected from the group consisting of pyrrolidino, hexamethyleneimino and piperidino; or a salt thereof, are well known in the art (see, e.g., U.S. Pat. No. 4,133,814). These compounds are known to be effective for the treatment of a variety of mammalian, particularly human, medical indications including, for example, postmenopausal osteoporosis and high serum cholesterol [see, e.g., Draper, et al., *Effects of Raloxifene (LY139481 HCl) on Biochemical Markers of Bone and Lipid Metabolism in Healthy Postmenopausal Women*, and Bryant, et al., *Protection from Bone Loss and Lowering of Serum Cholesterol in the Absence of Uterin Stimulation in Overiectomized Rats*, Am. Soc. Bone and Min. Res., Tampa, 9/18-22/93].

Compounds of formula I, and particularly acid salt forms of such compounds including, for example, hydrochloride, sulfate, hydrobromide, titrate, and the like, generally are poorly water soluble under ambient temperature. Because of this poor water solubility, it presently is necessary to administer these compounds as a suspension in water using a suspending agent such as carboxymethyl cellulose (CMC), polyethylene glycol, and the like. However, the present pharmaceutical formulations used with compounds of formula I cannot be utilized for many methods of administration.

Particularly, formulations useful for intravenous (IV) administration must be in the form of a solution. The IV administration of a suspension is extremely dangerous because particulate material in suspension can lodge in the microvasculature of a mammal causing life-threatening blockages and embolisms.

Water soluble formulations also are necessary for intranasal and aerosol administration of pharmaceutical agents because water solubility is necessary for such agents to cross upper and lower respiratory tract membranes. Failure to provide water soluble forms of these agents generally leads to poor drug absorption and/or irritation of the respiratory tract.

Additionally, it is desirable, although less critical, to have water soluble formulations available for other routes of administration. For example, liquid formulations for oral administration are desirable because they are more homogenous than other forms of pharmaceutical agents, and therefore, provide better dispersion and absorption in the GI tract. A water soluble formulation of a pharmaceutical agent also provides greater safety and convenience for a patient and the attending physician.

Although previous attempts of solubilizing compounds of formula I for use in pharmaceutical formulations generally have failed, the present invention provides novel aqueous solution inclusion complexes, pharmaceutical compositions thereof, and methods of using such complexes.

SUMMARY OF THE INVENTION

The present invention provides an aqueous solution inclusion complex comprising a compound of formula I above and a water soluble cyclodextrin.

Also provided by the present invention is a pharmaceutical composition comprising an aqueous solution inclusion complex as described above, in combination with a pharmaceutically acceptable carrier, diluent, or excipient.

The present invention further provides a method of inhibiting bone loss, as well as a method of lowering serum cholesterol levels, comprising administering an effective amount of the above-described inclusion complex to a mammal in need of such treatment.

DETAILED DESCRIPTION OF THE INVENTION

One aspect of the present invention provides an aqueous solution inclusion complex comprising a compound of formula I

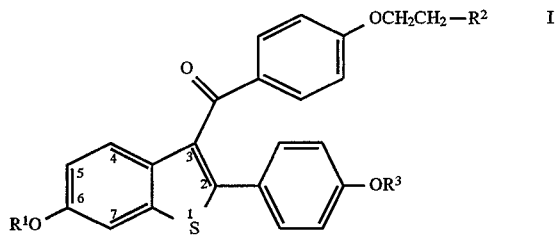

wherein $R^1$ and $R^3$ each are independently hydrogen, $C_1$-$C_4$ alkyl, —CO—($C_1$-$C_6$ alkyl), or —CO—Ar in which Ar is optionally substituted phenyl; and $R^2$ is selected from the group consisting of pyrrolidino, hexamethyleneimino and piperidino; or a salt thereof, and a water soluble cyclodextrin.

Compounds of formula I are well known in the art and can be prepared according to established procedures such as those detailed in U.S. Pat. Nos. 4,133,814, 4,418,068, and 4,380,635, each of which is herein incorporated by reference. In general, the process starts with a benzo[b]thiophene having a 6-hydroxyl group and a 2-(4-hydroxyphenyl) group. The starting compound is protected, alkylated or acylated, and deprotected to form the formula I compounds. Examples of the preparation of such compounds are provided in the U.S. patents discussed above.

The term "substituted phenyl" includes phenyl substituted once or twice with $C_1$-$C_6$ alkyl, $C_1$-$C_4$ alkoxy, hydroxy, nitro, chloro, fluoro, or tri(chloro or fluoro)methyl.

The term "alkyl", by itself or as part of another substituent, means a straight or branched chain alkyl radical having the stated number of carbon atoms such as, for example. methyl, ethyl, propyl, isopropyl, and the like, and higher homologs and isomers where indicated.

The term "alkoxy" means an alkyl group having the stated number of carbon atoms linked by an oxygen atom such as, for example, methoxy, ethoxy, propoxy, butoxy, pentyloxy, hexyloxy, and the like, and also includes branched chain structures such as, for example, isopropoxy and isobutoxy.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate,- methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumerate, glycolate, heptanoate, hippurate, lactate, malate, maleate, hydroxymaleate, melonate, mendelate, mesylate, nicotinate, isonicotinate, nitrate, oxalate, phthalate, terephthalate, phosphate, monohydrogenphosphate, dihydrogenphosphate, metephosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration, or the solvent can be stripped off by conventional means.

Bases commonly used for formation of phenolic salts include ammonium hydroxide and alkali and alkaline earth metal hydroxides, carbonates, as well as aliphatic and primary, secondary, and tertiary amines and aliphatic diamines. Bases especially useful in the preparation of addition salts include ammonium hydroxide, potassium carbonate, methylamine, diethylamine, ethylene diamine and cyclohexylamine.

For the purposes of the present invention, the preferred formula I compound is one in which each $R^1$ and $R^3$ is hydrogen, and $R^2$ is piperidino. Especially preferred is the hydrochloride salt form of this compound which is known in the art as Raloxifene.

Thus, compounds of formula I represent one of the starting materials of the present invention which, in the presence of the other starting material, a water soluble cyclodextrin, forms acqueous solution inclusion complexes of the present invention.

Cyclodextrins are cyclic molecules containing six or more α-D-glycopyranose units linked at the 1,4-positions by α linkages as in amylase. Because of this cyclic arrangement, the molecule is characterized as having neither a reducing end group nor a non-reducing end group. It is, therefore, believed that there is limited free rotation about the glycosidic bonds, and the cyclodextrins exist as conical-shaped molecules with the primary hydroxyls situated at the small end of the cone and the secondary hydroxyls situated at the large opening of the cone. The central cavity, formed by the conformation of the cyclic α-D-glycopyranose units, is lined by hydrogen atoms and oxygen atoms resulting in a relatively lipophilic cavity, but the outer surface is hydrophilic. Cyclodextrins, therefore, have the ability to form complexes with some organic and inorganic molecules.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Although this broad variety of cyclodextrins is described in the above patents and it is known that cylodextrins may be useful in preparing pharmaceutical agents for certain pharmaceutical delivery systems, it is also well recognized in the art that cyclodextrins will not assist in preparing such systems with all pharmaceutical agents.

Thus, use of cyclodextrins in the present invention is limited to water soluble cyclodextrins which form aqueous solutions upon the addition of water. The water solubility of cyclodextrins either is known in the art or may be determined via known procedures. Of the water soluble cyclodextrins, use of hydroxyalkyl-β-cyclodextrins (see, e g., U.S. Pat. No. 4,727,064) and, particularly, hydroxypropyl-β-cyclodexdrin, is preferred for preparing the inclusion complexes of the present invention.

Typically, the aqueous solution inclusion complexes of the present invention are prepared by adding water to the desired water soluble, synthesized or commercially available (see, e.g., Janssen Chimica, Geel, Belgium; Sigma Chemical Company, St. Louis, Mo.; Aldrich Chemical Company, Inc., Milwaukee, Wis.; Pharmtec, Alachuo, Fla.; and Lancaster Synthesis Inc., Windham, N.H.), cyclodextrin. Sufficient water, and preferably deionized water, is added so that the resulting concentration of cyclodextrin is from about 10% to about 50% (w/v), and preferably from about 15% to about 25% (w/v). Cyclodextrin concentrations of about 5% (w/v) or less are not desirable. The mixture of water and cyclodextrin is stirred until the solution becomes clear, and, thus, an aqueous cyclodextrin solution has been prepared.

Next, a compound of formula I is added to the above clear, aqueous solution of water and cyclodextrin and usually is sonicated for a short period of time, typically from about 1 to about 5 minutes. The resulting product is an aqueous solution inclusion complex of the present invention. The concentration of the desired formula I compound in the final inclusion complex is from about 0.1 mg/mL to about 20 mg/mL, preferably from about 5 mg/mL to about 15 mg/mL.

The preparation of aqueous solution inclusion complexes of the present invention usually is run at ambient temperature.

The pH of these inclusion complexes is slightly acidic to about neutral (from about 5.0 to about 7.0). The pH generally need not be adjusted prior to preparation of pharmaceutical compositions.

Thus, the present invention also provides pharmaceutical compositions comprising an aqueous solution inclusion complex of the present invention in combination with a pharmaceutically acceptable carrier, diluent, or excipient. Such pharmaceutical compositions are prepared in a manner well known in the pharmaceutical art, and are administered individually or in combination with other therapeutic agents, preferably via parenteral routes. An especially preferred route is intravenous. Other preferred routes of administration include oral, intranasal, and inhalation.

In making the compositions of the present invention, active ingredient, which comprises at least one aqueous solution inclusion complex of the present invention, is usually mixed with the excipient or diluted by an excipient. When an excipient is used as a diluent, it should be a liquid material which acts as a vehicle, carrier, or medium for the active ingredient.

Some examples of suitable excipients include water and syrup, and the formulations can additionally include wetting agents, preserving agents such as methyl- and propyl-hydroxybenzoates, additional sweetening agents, and flavoring agents.

The compositions are preferably formulated in a unit dosage form with each dosage normally containing from about 1 mL to about 100 mL, more usually from about 20 mL to about 60 mL of the active ingredient in aqueous solution. The term "unit dosage form" refers to physically discrete units suitable as unitary dosages for human subjects and other mammals, each unit containing a predetermined quantity of active material calculated to produce the desired therapeutic effect in association with a suitable pharmaceutical excipient.

The particular dosage of an aqueous solution inclusion complex of the present invention required to treat the aforementioned medical indications will depend upon the severity of the disease or condition, its route of administration, and related factors that will be decided by the attending physician. Generally, accepted and effective dosages will be from about 0.1 mg to about 1000 mg, and more typically, from about 50 mg to about 600 mg. Such dosages will be administered to a mammal in need of such treatment from about once to about three times a day.

The following formulation examples only are illustrative and are not intended to limit the scope of the present invention in any way.

FORMULATION 1

An intraveneous formulation may be prepared as follows:
100 mL of 20% cyclodextrin solution containing
100 mg/mL of a formula I compound;
and q.s. to 1000 mL of isotonic saline.

FORMULATION 2

An aerosol solution may be prepared containing the following components:
10 mL of 20% cyclodextrin solution containing
100 mg of a formula I compound;
25% ethanol; and
70% Propellant 22® (chlorodifluoromethane).

FORMULATION 3

An oral formulation may be prepared containing the following components
20 mL of 20% cyclodextrin solution containing
200 mg of a formula I compound.

Because previous attempts to adequately solubilize compounds of formula I generally have failed, we unexpectedly found that compounds of formula I would form aqueous solutions when added to a solution of a water soluble cyclodextrin in water.

Quite surprisingly, we further found that oral administration to monkeys of an aqueous solution inclusion complex of the present invention resulted in a greater than 15-fold increase in total blood plasma levels of a formula I compound, particularly Raloxifene, compared to the administration of an equal dosage prepared as a wet granular formulation.

The aqueous solution inclusion complexes of the present invention are effective for the treatment of postmenopausal osteoporosis. Thus, the present invention further provides a method for inhibiting bone loss comprising administering to a mammal, particularly a postmenopausal woman, in need of treatment an effective amount of an aqueous solution inclusion complex of the present invention.

The aqueous solution inclusion complexes of the present invention also are effective for the treatment of high serum cholesterol. The present invention, therefore, also provides a method for lowering serum cholesterol levels comprising administering to a mammal, particularly a human, in need of treatment an effective amount of an aqueous solution inclusion complex of the present invention.

The following example is provided to further illustrate the present invention. It is not intended that the invention be limited in scope by reason of any of the following example.

EXAMPLE 1

Preparation of Raloxifene-Hydroxypropyl-β-Cyclodextrin Inclusion Complex

A 20% (w/v) solution of hydroxypropyl-β-cyclodextrin was prepared by adding 500 mL of deionized water to 100 gm of hydroxypropyl-β-cyclodextrin. The mixture was stirred until it became a clear solution. To a 50 mL aliquot of the above solution was added 500 mg of Raloxifene and the resulting solution was placed in a sonicator for 3 minutes. The resulting inclusion complex is a clear, yellow, aqueous solution.

We claim:

1. An aqueous solution inclusion complex comprising a compound of formula I wherein
$R^1$ and $R^3$ each are independently hydrogen, $C_1$–$C_4$ alkyl, —CO—($C_1$–$C_6$ alkyl), or —CO—Ar in which Ar is optionally substituted phenyl; and $R^2$ is selected from the group consisting of pyrrolidino, hexamethyleneimino and piperidino;

or a salt thereof, and hydroxypropyl-β-cyclodextrin.

2. An inclusion complex of claim 1 wherein $R^2$ is piperidino, and $R^1$ and $R^3$ each are hydrogen.

3. An inclusion complex of claim 2 wherein said salt is a hydrochloride salt.

4. An inclusion complex of claim 3 wherein the concentration of a formula I compound constitutes from about 0.1 mg/mL to about 20 mg/mL.

5. An inclusion complex of claim 4 wherein said concentration of a formula I compound constitutes from about 5 mg/mL to about 10 mg/mL.

6. An inclusion of claim 3 wherein the concentration of said hydroxypropyl-β-cyclodextrin constitutes from about 10% to about 50% (w/v).

7. An inclusion complex of claim 6 wherein said concentration of said hydroxypropyl-β-cyclodextrin constitutes from about 15% to about 25% (w/v).

8. An inclusion complex of claim 7 wherein the concentration of a formula I compound constitutes from about 5 mg/mL to about 10 mg/mL.

9. A pharmaceutical composition comprising an inclusion complex according to claim 1 in combination with a pharmaceutically acceptable carrier, diluent or excipient.

10. A pharmaceutical composition according to claim wherein $R^1$ and $R^3$ of said compound of formula I each are hydrogen, $R^2$ of said compound is piperidino, and said salt is a hydroichloride salt.

11. A method of inhibiting bone loss comprising administering to a mammal in need of treatment an effective amount of an inclusion complex of claim 1.

12. A method according to claim 11 wherein $R^1$ and $R^3$ of said compound of formula I each are hydrogen, and $R^2$ of said compound is piperidino, and said salt is a hydrocloride salt.

13. A method according to claim 12 wherein said mammal is a postmenopausal woman.

14. A method of lowering serum cholesterol levels comprising administering to a mammal in need of treatment an effective amount of an inclusion complex of claim 1.

15. A method according to claim 14 wherein $R^1$ and $R^3$ of said compound of formula I each are hydrogen, and $R^2$ of said compound is piperidino.

16. A method according to claim 15 wherein said mammal is a human.

\* \* \* \* \*

UNITED STATES PATENT AND TRADEMARK OFFICE
CERTIFICATE OF CORRECTION

PATENT NO. : 5,624,940

DATED : April 29, 1997

INVENTOR(S) : Henry U. Bryant, et. al.

It is certified that error appears in the above-indentified patent and that said Letters Patent is hereby corrected as shown below:

Column 1, line 8 reads ... "of prior" ... should read - of pending prior -

Column 8, line 1 reads ... "to claim" ... should read - to claim 9 -

Signed and Sealed this

Twenty-fifth Day of November, 1997

Attest:

BRUCE LEHMAN

Attesting Officer

Commissioner of Patents and Trademarks